(12) United States Patent
Rajaiah et al.

(10) Patent No.: US 6,719,995 B2
(45) Date of Patent: *Apr. 13, 2004

(54) SYSTEMS FOR DELIVERING A COSMETIC AND/OR THERAPEUTIC ACTIVE TO ORAL SURFACES USING AN INTEGRAL CARRIER

(75) Inventors: Jayanth Rajaiah, Loveland, OH (US); Lisa Catron Ernst, Cincinnati, OH (US); Ann Maria Case, Cincinnati, OH (US); Thinh Nguyen Ha, Cincinnati, OH (US); William Michael Glandorf, Mason, OH (US); Christopher Robert Mayer, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/241,990

(22) Filed: Dec. 18, 2002

(65) Prior Publication Data

US 2003/0113276 A1 Jun. 19, 2003

Related U.S. Application Data

(63) Continuation of application No. 10/084,896, filed on Feb. 28, 2002, now Pat. No. 6,514,484
(60) Provisional application No. 60/276,977, filed on Mar. 19, 2001.

(51) Int. Cl.[7] .................. A61K 31/385; A61K 31/70
(52) U.S. Cl. .................. 424/435; 424/401; 424/443; 424/49; 424/50; 424/51; 424/52; 424/53; 424/54; 424/55; 424/56; 424/57; 424/58; 523/105; 523/109; 523/118

(58) Field of Search .................. 424/49–58, 435, 424/443, 401; 523/105, 109, 118

(56) References Cited

U.S. PATENT DOCUMENTS

| 3,955,281 A | 5/1976 | Weitzman |
| 4,138,814 A | 2/1979 | Weitzman |

(List continued on next page.)

FOREIGN PATENT DOCUMENTS

| GB | 1 108 841 A | | 5/1983 |
| JP | 63-54318 | | 3/1988 |
| JP | 10-17448 | | 1/1998 |
| WO | WO 97/25968 | | 7/1997 |
| WO | WO 99/62472 | | 12/1999 |
| WO | 2002074099 | * | 9/2002 |
| WO | 2002074263 | * | 9/2002 |
| WO | 2002074274 | * | 9/2002 |
| WO | 2002074275 | * | 9/2002 |
| WO | 2002074276 | * | 9/2002 |

*Primary Examiner*—Frederick Krass
(74) *Attorney, Agent, or Firm*—Emelyn DeLeon Hiland; Andrea L. Winslow; Betty J. Zea

(57) ABSTRACT

Systems for delivering cosmetic and therapeutic actives to the oral cavity employ a strip comprising a first layer of material, a second layer comprising polybutene with a molecular weight of about 300 to about 3000, and a cosmetic or therapeutic active included within the second layer. Therapeutic and cosmetic actives in compositions comprising polybutene inhibit or prevent gingivitis, caries, staining, fungi, bacteria and plaque build-up in the oral cavity by means of the delivery system.

24 Claims, 4 Drawing Sheets

U.S. PATENT DOCUMENTS

| | | |
|---|---|---|
| 4,324,547 A | 4/1982 | Arcan et al. |
| 4,554,154 A | 11/1985 | White |
| 4,728,291 A | 3/1988 | Golub |
| 4,741,941 A | 5/1988 | Englebert et al. |
| 4,786,253 A | 11/1988 | Morais |
| 4,799,888 A | 1/1989 | Golub |
| 4,900,554 A | 2/1990 | Yanagibashi et al. |
| 5,114,718 A | 5/1992 | Damani |
| 5,166,233 A | 11/1992 | Kuroya et al. |
| 5,185,386 A | 2/1993 | Cohen et al. |
| 5,310,563 A | 5/1994 | Curtis et al. |
| 5,326,685 A | 7/1994 | Gaglio et al. |
| 5,340,314 A | 8/1994 | Tarvis |
| 5,496,541 A | 3/1996 | Cutler |
| 5,560,379 A | 10/1996 | Pieczenik |
| 5,639,445 A | 6/1997 | Curtis et al. |
| 5,713,738 A | 2/1998 | Yarborough |
| 5,880,172 A | 3/1999 | Rajaiah et al. |
| 5,891,453 A | 4/1999 | Sagel et al. |
| 5,900,230 A | 5/1999 | Cutler |
| 6,491,896 B1 * | 12/2002 | Rajaiah et al. |
| 6,500,406 B1 * | 12/2002 | Rajaiah et al. |
| 6,509,007 B2 * | 1/2003 | Rajaiah et al. |
| 6,514,484 B2 * | 2/2003 | Rajaiah et al. |

* cited by examiner

SYSTEMS FOR DELIVERING A COSMETIC AND/OR THERAPEUTIC ACTIVE TO ORAL SURFACES USING AN INTEGRAL CARRIER

CROSS-REFERENCE TO RELATED APPLICATIONS

This application is a continuation of U.S. Ser. No. 10/084,896, filed Feb. 28, 2002, now U.S. Pat. No. 6,514,484, which claims the benefit of U.S. Provisional Application No. 60/276,977, filed Mar. 19, 2001.

FIELD OF THE INVENTION

The present invention relates to systems for delivering cosmetic and therapeutic benefits to the oral cavity by applying low molecular weight polybutene to the teeth by means of an integral carrier, in one embodiment, a strip of material.

BACKGROUND OF THE INVENTION

Dental products by which various cosmetic and/or therapeutic actives are delivered to teeth and oral cavity have been previously known. Examples of such products include: brushing aids such as dentifrice products for delivery of anti-caries actives like fluoride; effervescent denture cleansing tablets, which require the artificial teeth to soak for a period of time, to remove plaque and debris; and mouthwashes containing breath fresheners or antibacterial actives. However, such conventional dental care products typically do not maintain actives in the oral cavity long enough to optimally enhance or prolong their therapeutic, prophylactic and/or cosmetic benefits.

The use of a dental strip has been recognized as a convenient and inexpensive way to deliver cosmetic and therapeutic benefits to the teeth and mucosal surfaces of the oral cavity. For example, dental whitening strips, where a whitening composition is applied to a strip and thereafter applied to the teeth to achieve sustained contact between the teeth and the oral care active, such as in WO 99/62472 to Wolf are known. However, these applications often employ elastomeric polymers as an adhesive, second layer. Such adhesives provide sustained release of an active but can result in a thick, gummy residue remaining in the mouth when the strip is removed from the teeth.

In order to provide a composition that achieves improved substantivity without leaving behind unwanted buildup of adhesive on the teeth and oral mucosa, the use of lower molecular weight polybutene applied by means of an integral carrier, in one embodiment a strip of material, is herein disclosed.

Polybutene is known as a component of denture adhesives and as a gum base. For example, U.S. Pat. No. 5,880,172, issued Mar. 3, 1999, to Rajaiah, et al., discloses a self-supporting denture adhesive that is peelable for easy removal, which incorporates polybutene as an optional ingredient. Also, U.S. Pat. No. 5,496,541, issued Mar. 5, 1996, to Cutler, relates to a dentifrice chewing gum and teaches the use of polybutene as an optional gum base. However, such applications often employ a non-flowable, high molecular weight polybutene in order to achieve the sought after benefits.

In the present invention, lower molecular weight polybutene and a cosmetic or therapeutic active are used in combination with a dental strip delivery system to provide a protective coating on the teeth. The lower molecular weight polybutene is a flowable liquid that is extremely substantive when applied to the teeth yet does not stick to the soft tissue of the oral cavity. The polybutene coating inhibits and prevents staining of the teeth and is suitable for delivering an active to treat the oral cavity. Upon removal of the strip from the teeth, unwanted gummy residue or buildup of the composition on the teeth and oral mucosa does not occur.

SUMMARY OF THE INVENTION

The present invention relates to systems for delivering a cosmetic or therapeutic active to the teeth and oral cavity using an integral carrier. In one embodiment the delivery system comprises: a first layer of a strip material; a second layer comprising polybutene with a molecular weight of about 300 to about 3000 releasably associated to the said strip material; and a cosmetic or therapeutic active associated with said second layer. The present invention is used to deliver therapeutic and cosmetic benefits to the oral cavity by directly applying the integral carrier to the teeth. The integral carrier may be of sufficient size that, once applied, the integral carrier overlaps with the oral soft tissues. This renders the system useful for delivering cosmetic and therapeutic actives directly to the gingival tissue, as well as the teeth.

The cosmetic and therapeutic actives incorporated within the second layer of the delivery system can be selected from the group consisting of anti-calculus agents, fluoride ion sources, stannous ion sources, whitening agents, anti-microbial, anti-plaque agents, anti-inflammatory agents, nutrients, antioxidants, anti-viral agents, anti-fungal agents, analgesic and anesthetic agents, H-2 antagonists, fragrances and sensates, components other than polybutene which deliver a clean feel to the teeth, pigments dyes, lakes and colorants, and mixtures thereof. When desired a viscosity modifier may optionally be incorporated in the second layer.

The present invention also relates to a method of delivering therapeutic and cosmetic actives to the oral cavity or teeth by using the delivery system herein to apply a composition comprising polybutene with a molecular weight of about 300 to about 3000 and one or more therapeutic or cosmetic actives to the teeth or hard surfaces of the oral cavity. Also disclosed is a method for inhibiting or preventing gingivitis, caries staining, fungi and bacteria and plaque build up in the oral cavity by using the delivery system disclosed herein to apply a composition comprising lower molecular weight polybutene (molecular weight from about 300 to about 3000) and a therapeutic or cosmetic active.

BRIEF DESCRIPTION OF THE DRAWINGS

While the specification concludes with claims that particularly point out and distinctly claim the present invention, it is believed that the present invention will be understood better from the following description of preferred embodiments, taken in conjunction with the accompanying drawings, in which like reference numerals identify identical elements. In one embodiment of the present invention, the integral carrier comprises a strip of material. Without intending to limit the invention, this embodiment is described in more detail below:

DETAILED DESCRIPTION OF THE INVENTION

Figure 1:
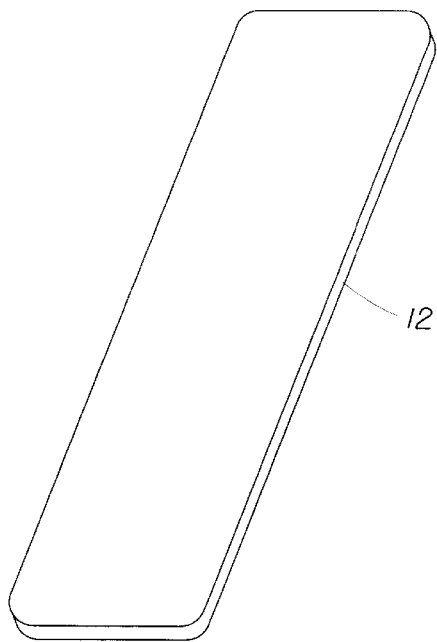
FIG. 1 is a perspective view of a substantially flat strip of material having rounded corners.

The present invention relates to systems for delivering cosmetic and therapeutic actives to the teeth and oral cavity use of an integral carrier comprising: a first layer of a carrier material; a second layer comprising polybutene with a molecular weight of about 300 to about 3000 releasably associated to the said strip material; and a cosmetic or therapeutic active associated with said second layer.

Definitions

The term "teeth", as used herein, is meant to include natural teeth, dentures, dental plates, fillings, caps, crowns, bridges, dental implants, and the like, and any other hard surfaced dental prosthesis either permanently or temporarily fixed within the oral cavity.

By "safe and effective amount", as used herein, is meant an amount of an agent (e.g., anti-calculus agent) high enough to significantly improve the condition to be treated, but low enough to avoid serious side effects (at a reasonable benefit/risk ratio), within the scope of sound medical/dental judgment. The safe and effective amount of an agent (e.g., anti-calculus agent) may vary with the particular condition being treated, the age and physical condition of the patient being treated, the severity of the condition, the duration of treatment, the nature of concurrent therapy, the specific form of the source employed, and the particular vehicle from which the agent is applied.

The term "non-self supporting" is used to describe a composition that lacks integrity and strength. In the instant case, this means that the composition is unable to be detached as one solid piece from the teeth even after several hours of use in the mouth. The composition cannot be cut and formed into definite shapes, such as a sheet or cone, which maintain their initial dimensions.

The term "mucoadhesive" or "bioadhesive" as used herein refers to the phenomenon where a natural or synthetic substance applied to a wet mucosal epithelium adheres, usually creating a new interface, to the mucous layer. (*CRC Critical Review in Ther. Drug Carrier*, Vol.5, Issue 1, p.21 (1988)). Generally mucoadhesion can be achieved via physical or chemical processes or both. This mechanism is described in *Journal of Controlled Release*, Vol.2, p257 (1982) and *Journal of Controlled Release*, Vol.18 (1992) p. 249. The above references are incorporated by reference herein in their entirety.

"Tartar" and "calculus" are used interchangeably and refer to mineralized dental plaque biofilms.

The term "unit dose form" refers to physically discrete units suitable as unitary dosages for human subjects and other mammals, each containing a predetermined quantity of active material calculated to produce the desired therapeutic effect.

The term "viscosity" as used herein refers to kinematic viscosity, measured using the standard test method for Kinematic Viscosity of Transparent and Opaque Liquids (the Calculation of Dynamic Viscosity), ASTM D-445. As reported, viscosity is measured at 99° C. (210° F.) unless otherwise indicated. A sample is placed in a U-shaped "Cannon-Fenske" type viscometer (for transparent liquids) tube and submerged into a constant temperature bath. Flow is timed between two marks on the tube and viscosity is determined by simple calculations dependent on time and a standard factor supplied by the tube manufacturer.

"Molecular weight", as referred to herein, is reported as a number average, determined using gel permeation chromatography. The number average molecular weight, or arithmetic mean, is a function of the number of molecules in a given mass of polymer. It is represented by the formula:

$$M_n = \frac{\Sigma N_i M_i}{\Sigma N_i} = \frac{\Sigma n_i M_i}{}$$

where $N_i$, represents the number of molecules present for a given molecular weight, $M_i$ and $n_i = N_i/\Sigma N_i$ is the number fraction of molecular weight, $M_i$.

Percentages and ratios herein are by weight of total composition, unless otherwise indicated.

I. First Layer

The first layer of the present invention comprises an integral carrier, in one embodiment a strip of material, in a delivery system for cosmetic and therapeutic actives in the oral cavity.

Figure 2:
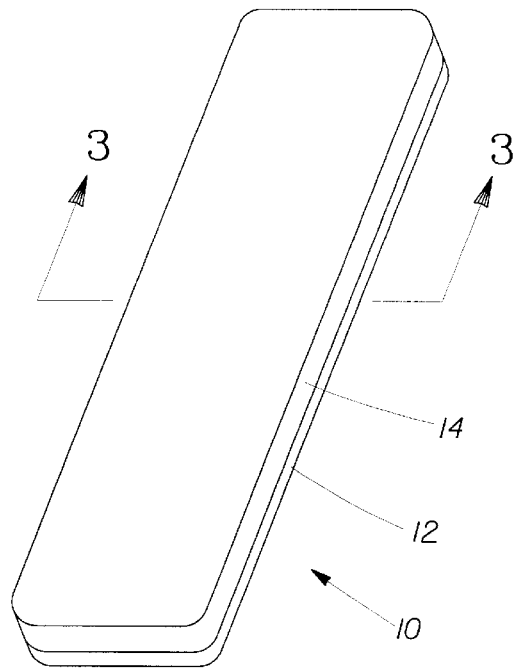
FIG. 2 is a perspective view of an embodiment of the present invention, disclosing the strip of FIG. 1 upon which a second layer composition comprising polybutene with a molecular weight of about 300 to about 3000 and a cosmetic or therapeutic active for treating teeth and gums is releaseably associated.

Referring now to the drawings, and more particularly to FIGS. 1 and 2, there is shown a first embodiment of the present invention, generally indicated as 10, representing a delivery system for delivering cosmetic and therapeutic actives to the teeth and oral cavity. Delivery system 10 has a strip of material 12, which is substantially flat, preferably with rounded corners.

Figure 3:
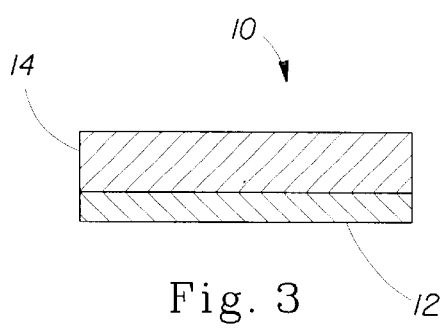
FIG. 3 is a cross-sectional view, taken along section line 3—3 of FIG. 2, showing an example of the strip of material having a thickness less than that of the second layer coated thereon.

Releasably applied onto said strip of material 12 is a second layer composition 14. Second layer composition 14 is homogenous, and may be uniformly and continuously coated onto strip of material 12, as shown in FIG. 3. However, second layer composition 14 may alternatively be a laminate or separated layers of components, an amorphous mixture of components, separate stripes or spots or other patterns of different components, or a combination of these structures including a continuous coating of second layer composition 14 along a longitudinal axis of a portion of strip of material 12.

Figure 4:
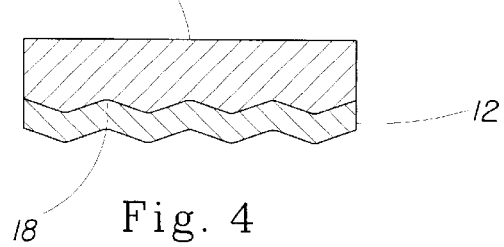
FIG. 4 is a cross-sectional view, showing an alternative embodiment of the present invention, showing shallow pockets in the strip of material, which act as reservoirs for additional amounts of the second layer coated on the strip.

As shown in FIG. 4 in an alternative embodiment, strip of material 12 may have shallow pockets 18 formed therein. When second layer composition 14 is coated on a strip of material 12, additional second layer composition 14, if present, fills shallow pockets 18 to provide reservoirs of second layer composition 14.

Figure 5:
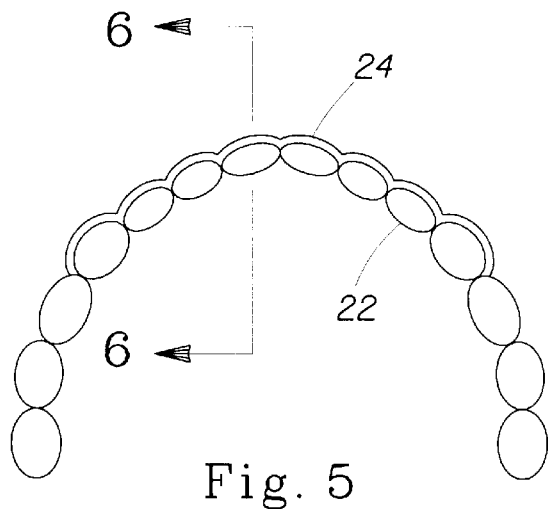
FIG. 5 is a cross-sectional plan view, showing an alternative embodiment for applying the second layer composition to adjacent teeth having the strip of material of the present invention conforming thereto and adhesively attached to the teeth by means of the second layer composition located between the teeth and the strip of material.
Figure 6:
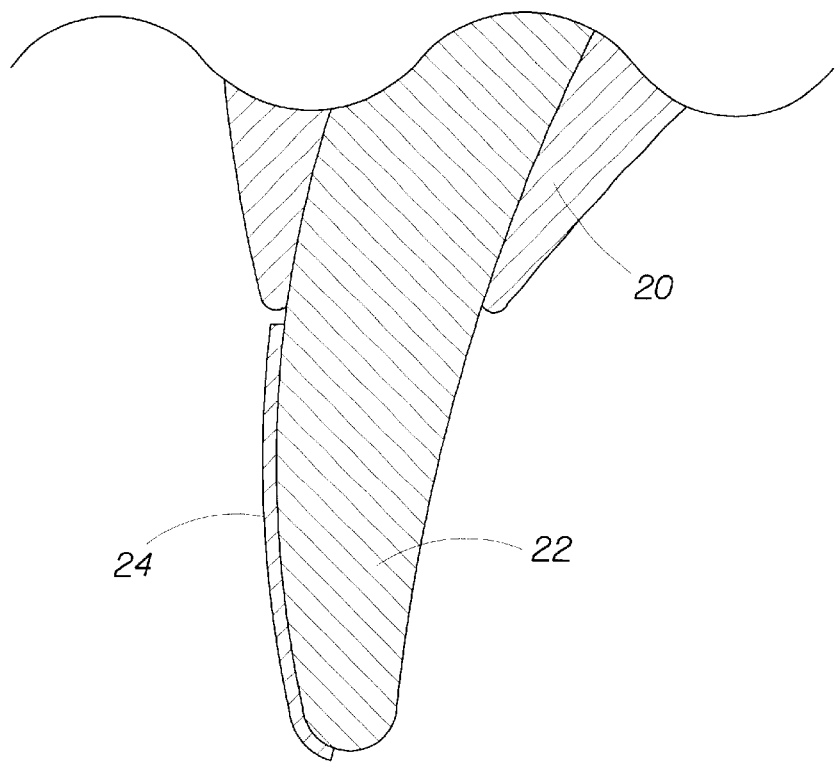
FIG. 6 is a cross-sectional elevation view of a tooth, taken along section line 6—6 of FIG. 5, showing the strip of material of the present invention conforming to and adhesively attached to the teeth by means of the oral care substance located between the teeth and strip of material.

FIGS. 5 and 6 show a delivery system 24 of the present invention applied to the surface of a tooth and plurality of adjacent teeth. Embedded in adjacent soft tissue 20 are a plurality of adjacent teeth 22. Adjacent soft tissue herein defined as soft tissue surfaces surrounding the tooth structure including: papilla, marginal gingival, gingival sulculus, inter dental gingival, and gingival gum structure on lingual and buccal surfaces up to and including muco-gingival junction on the pallet.

In both FIGS. 5 and 6, delivery system 24 represents strip of material 12 and second layer composition 14, with second layer composition 14 on the side of strip material 12 facing tooth 22. Second layer composition 14 may be pre-applied to strip of material 12, or may be applied to strip of material 12 by the user prior to application to the teeth. In an alternate embodiment, the second layer composition may be applied directly to teeth 22 by the user and then covered by a strip of material 12. In any case, strip of material 12 has a thickness and flexural stiffness such that it can conform to the contoured surfaces of tooth 22 and to adjacent soft tissue 20. Preferably, the strip of material has sufficient flexibility to form to the contours of the oral surface, the surface being a plurality of adjacent teeth. The strip of material is also readily conformable to tooth surfaces and to the interstitial tooth spaces without permanent deformation when the delivery system is applied. The delivery system can be applied without significant pressure.

Figure 7:
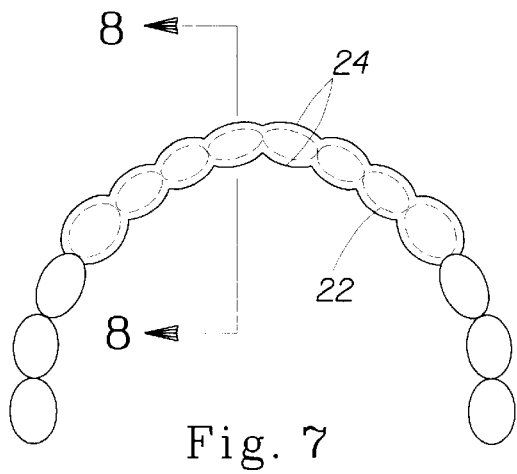
FIG. 7 is a cross-sectional plan view, similar to FIG. 5, showing a strip of material of the present invention conforming to the teeth and the adjoining soft tissue and adhesively attached to both sides of the teeth by means of the second layer composition located between the teeth and the strip of material.
Figure 8:
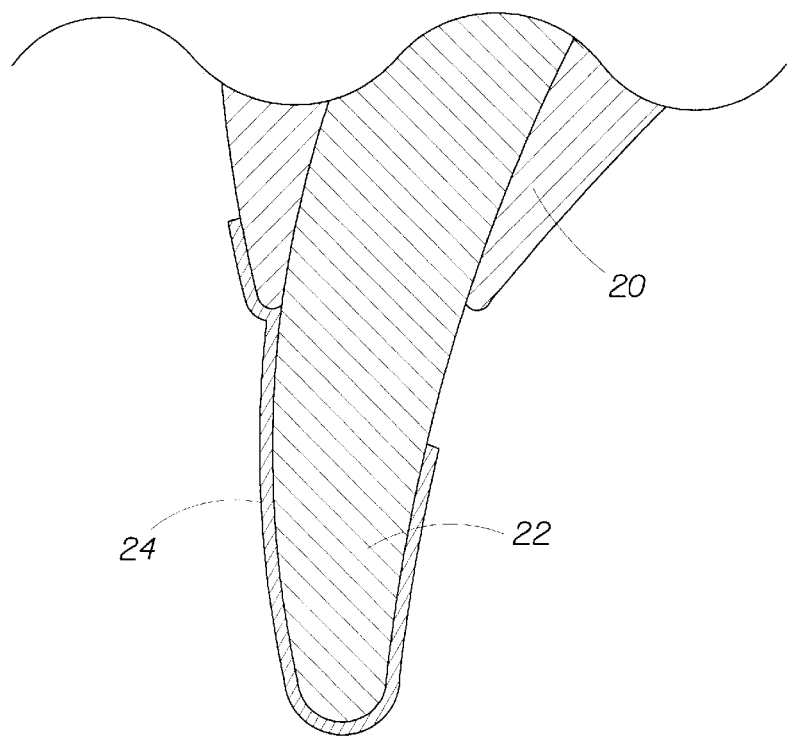
FIG. 8 is a cross-sectional elevation view, taken along section line 8—8 of FIG. 7, showing a strip of material of the present invention conforming to both the tooth and the adjoining soft tissue and adhesively attached to both sides of the tooth by means of the second layer composition located between the tooth and the strip of material.

FIGS. 7 and 8 show a delivery system 24 of the present invention applied to both front and rear surfaces of a plurality of adjacent teeth 22 as well as to adjacent soft tissue 20. Delivery system 24 represents strip of material 12 and second layer composition 14, with second layer composition 14 on the side of strip of material 12 facing tooth 22.

Figure 9:
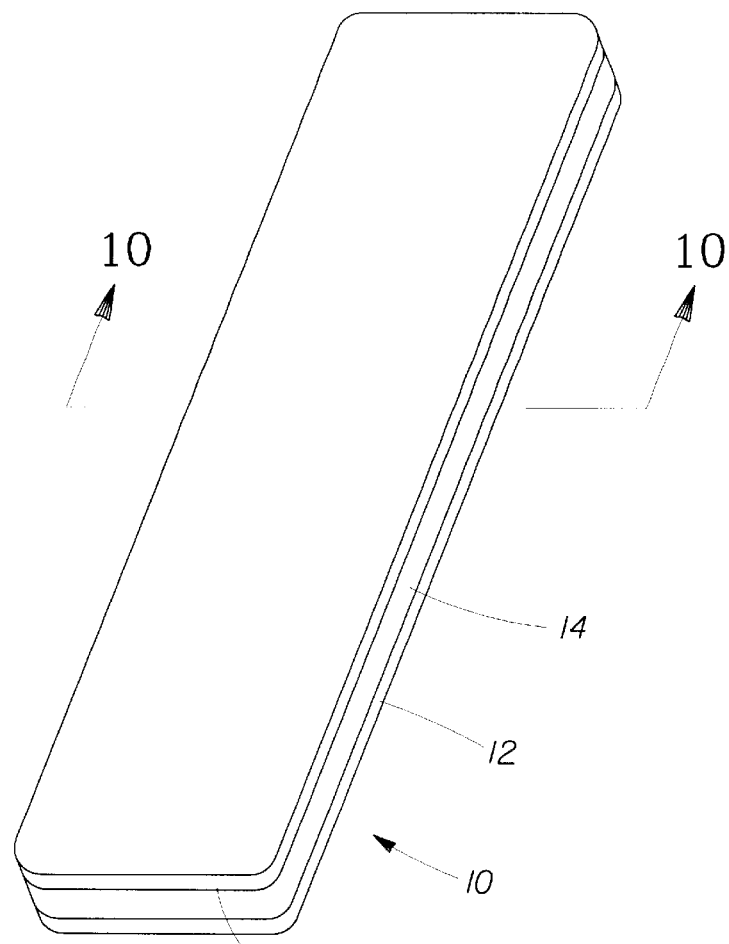
FIG. 9 is a perspective view of an alternative embodiment of the present invention, disclosing the strip of material coated with a second layer composition of FIG. 2 for treating teeth and adjoining soft tissue having a release liner.
Figure 10:
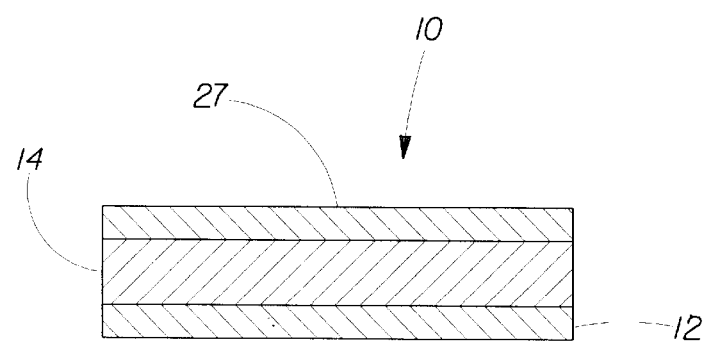
FIG. 10 is a cross-sectional view of an alternative embodiment of the present invention, taken along section line 10—10 of FIG. 9, showing a release liner attached to the strip of material by the second layer composition on the strip of the material.

FIGS. 9 and 10 shows an optional release liner 27. Release liner 27 is attached to strip of material 12 by second layer composition 14. Second layer composition 14 is on the side of strip material 12 facing release liner 27. This side is applied to the tooth and gum surfaces once release liner 27 is removed.

The first layer of the delivery system of the present invention is comprised of a strip of material. Such first layer materials are described in more detail in U.S. Pat. Nos. 6,136,297; 6,096,328; 5,894,017; 5,891,453; and 5,879,691, all to Sagel, et al., and all assigned to The Procter & Gamble Company, all incorporated herein by reference in their entirety and in U.S. Pat. Nos. 5,989,569 and 6,045,811 both to Dirksing, et al., and both assigned to The Procter & Gamble Company, also both incorporated herein by reference in their entirety.

The strip serves as a protective barrier for the oral care substance. It prevents leaching and/or erosion of the second layer by for example, the wearer's tongue, lips, and saliva. This allows the active in the second layer to act upon the hard surfaces of the oral cavity for an extended period of time, from several minutes to several hours.

The strip material may comprise polymers, natural and synthetic woven materials, non-woven material, foil, paper, rubber and combinations thereof. The strip material may be a single layer of material or a laminate of more than one layer. Regardless of the number of layers, the strip of material is substantially water insoluble. The strip may also be water impermeable. In one embodiment the material is any type of polymer or combination of polymers that meet the required flexural rigidity and are compatible with oral care substances. Suitable polymers include, but are not limited to, polyethylene, ethylvinylacetate, polyesters, ethylvinyl alcohol and combinations thereof. Examples of polyesters include Mylar® and fluoroplastics such as Teflon®, both manufactured by Dupont. In one embodiment the material is polyethylene. The strip of material is generally less than about 1 mm (millimeter) thick, in one embodiment less than about 0.05 mm thick, in yet another embodiment from about 0.001 to about 0.03 mm thick. A polyethylene strip of material is generally less than about 0.1 mm thick and in one embodiment from about 0.005 to about 0.02 mm thick.

The shape of the strip of material is any shape and size that covers the desired oral surface. In one embodiment the strip has rounded corners to avoid irritation of the soft tissue of the oral cavity. "Rounded corners," means not having any sharp angles or points. In one embodiment, the length of the strip material is from about 2 cm (centimeter) to about 12 cm, in another embodiment from about 4 cm to about 9 cm. The width of the strip material will also depend on the oral surface area to be covered. The width of the strip is generally from about 0.5 cm to about 4 cm, in one embodiment from about 1 cm to about 2 cm. In yet another embodiment, the strip may be worn as a patch on one or several teeth to treat a localized condition.

The strip material may contain shallow pockets. When the cosmetic or therapeutic active is coated on a strip of material, additional cosmetic and therapeutic active fills shallow pockets to provide reservoirs of additional cosmetic and therapeutic active. Additionally the shallow pockets help to provide texture to the delivery system. In one embodiment the film will have an array of shallow pockets. Generally the shallow pockets are approximately 0.4 mm across and about 0.1 mm deep. When shallow pockets are included in the strip of material and oral care substances are applied to it in various thicknesses, the overall thickness of the delivery system is less than about 1 mm. In one embodiment the overall thickness is less than about 0.5 mm.

Flexural stiffness is a material property that is a function of a combination of strip thickness, width and material modulus of elasticity. This test is a method for measuring the rigidity of polyolefin film and sheeting. It determines the resistance to flexure of a sample by using a strain gauge affixed to the end of a horizontal beam. The opposite end of the beam presses across a strip of the sample to force a portion of the strip into a vertical groove in a horizontal platform upon which the sample rests. A microammeter wired to the strain gauge is calibrated in terms of deflection force. The rigidity of the sample is read directly from the microammeter and expressed as grams per centimeter of the sample strip width. In the present invention, the strip of material has a flexural stiffness of less than about 5 grams/cm as measured on a Handle-O-Meter, model #211-300, available from Thwing-Albert Instrument Company of Philadelphia, Pa. as per test method ASTM D2923-95. In one embodiment the strip has a flexural stiffness less than about 3 grams/cm, in another embodiment less than about 2 grams/cm and in yet another embodiment from about 0.1 to about 1 grams/cm. Generally, the flexural stiffness of the strip of material is substantially constant and does not change during normal use. For example, the strip of material does not need to be hydrated for the strip to achieve the low flexural stiffness in the above-specified ranges.

This relatively low stiffness enables the strip of material to cover the contours of the oral surface with very little force being exerted. That is, conformity to the contours of the oral surface of the wearer's mouth is maintained because there is little residual force within the strip of material to cause it to return to its shape just prior to its application to the oral surface, i.e. substantially flat. The strip of material's flexibility enables it to contact soft tissue over an extended period of time without irritation. The strip of material does not require continuous pressure for retention against the oral surface.

The strip of material is held in place on the oral surface by adhesive attachment provided by the polybutene. The viscosity and general tackiness of the polybutene to dry surfaces cause the strip to be adhesively attached to the oral surface without substantial slippage from the frictional forces created by the lips, teeth, tongue, and other oral surfaces rubbing against the strip of material while talking, drinking, etc. However, this adhesion to the oral surface is low enough to allow the strip of material to be easily removed by the wearer by simply peeling off the strip of material using one's finger. The delivery system is easily removable from the oral surfaces without the use of an instrument, a chemical solvent or agent or excess friction.

II. Second Layer

Polybutene

Polybutene is a viscous copolymer of isobutylene and butene monomers. "Polybutene", as used herein, refers to both hydrogenated (CAS #68937-10-0) and unhydrogenated (CAS #9003-29-6) forms of the polymer. Polybutene is a viscous, colorless, non-drying, liquid polymer. Polybutenes range from flowable liquids to near semi-solid states. Polybutenes are clear, odorless, chemically stable, resistant to oxidation by light and heat, non-toxic and non-hazardous.

The second layer of present invention comprises polybutene, generally of a lower molecular weight from about 300 to about 3000, in another embodiment from about 500 to about 2200 and in another embodiment from about 750 to about 1500. The viscosity of the polybutene disclosed herein, ranges from about 30 cSt (centi Stoke) measured at 38° C. to about 4,500 cSt measured at 99° C., in another embodiment from about 200 cSt measured at 38° C. to about 3,500 cSt measured at 99° C., and in another embodiment 75 cSt measured at 99° C. to about 700 cSt measures at 99° C. Polybutene is included from about 0.01% to about 100%, by weight of the second layer, in another embodiment from about 1% to about 100%, in yet another embodiment from about 50% to about 100%.

The polybutene of the present invention does not exhibit elastomeric properties. Elastomers are amorphous polymers that have the ability to stretch out and spring back to their original shapes. Such elastomeric polymers must have a modest amount of cross-linking to prevent the polymeric chains from slipping over one another, and the chains must have an irregular shape to prevent the formation of crystalline regions within the polymeric chains. Synthetic elastomers, are described in more detail in Kirk-Othmer, *Encyclopedia of Chemical Technology*, Fourth Edition, Volume 8, Wiley-Interscience Publishers (1996), pages 934–955, incorporated herein by reference, including all references incorporated into Kirk-Othmer. The polybutene of the present invention is not cross-linked and does not exhibit rubbery or elastic behavior. When subjected to a stretching or bending force, the polybutene herein does not return to its original shape upon the removal of the force.

Lower molecular weight polybutene (Molecular Weight= 300–3000), which is a flowable liquid known for its adhesive properties, is actually non-mucoadhesive. That is, the polybutene, while displaying excellent adhesion properties on the hard surfaces of the oral cavity, will not significantly adhere to the mucosa or wet, soft tissue of the mouth. In fact, polybutene is extremely substantive when applied to the teeth, denture, dental plate, dental implant or other hard surface of the oral cavity, making it suitable for once daily application and treatment of the artificial teeth. High retention of the polybutene is achieved, even when thorough brushing of the hard surfaces has occurred. Thus, the polybutene, once applied to the tooth surface, is long lasting, and rinse resistant, which allows for sustained release of cosmetic and therapeutic actives. Importantly, the second layer of the present invention is not self-supporting neither before, during, or after application to the teeth.

Once applied to the teeth, the polybutene has a very smooth, slick texture, perceived by the consumer as a desirable, clean feeling. The polybutene acts as a lubricant on the hard surfaces, reducing the friction normally produced when the tongue slides over these surfaces.

Suitable polybutenes for use herein include, but are not limited to: Indopol L-14, Molecular Weight ("MW")=370; Indopol L-50, MW=455; Indopol L-65, MW=435; Indopol L-100, MW=510, H-15, MW=600; H-25, MW=670; H-35, MW=725; H-40, MW=750; H-50, MW=815; H-100, MW=940; H-300, MW=1330; H-1500, MW=2145; H-1900, MW=2270; Panalane L-14E, MW=370; Panalane H-300E, MW=1330; all trade names of BP Amoco Chemicals (Chicago, Ill.). Other suitable grades of polybutene include Parapol 450, MW=420; Parapol 700, MW=700; Parapol 950, MW=950; Parapol 1300, MW=1300; and Parapol 2500, MW=2700; all trade names of ExxonMobil Corporation.

Cosmetic and/or Therapeutic Actives

The present invention relates to a system for delivering cosmetic and therapeutic actives to the teeth and oral cavity by the use polybutene with an integral carrier comprising. In one embodiment the delivery system comprises: a first layer of a strip of material; and a second layer comprising polybutene with a molecular weight from about 300 to about 3000 releasably associated to the said strip material and a cosmetic or therapeutic active associated with the second layer. The second layer composition of the present invention may contain one or more cosmetic and/or therapeutic actives in unit dose form where, upon directed use, the benefit sought by the wearer is promoted. Examples of the oral conditions these actives address include, but are not limited to, whitening, stain bleaching, stain removal, other appearance and structural changes to teeth, and treatment and prevention of plaque, tartar, cavities, inflamed and/or bleeding gums, gingivitis, fungal infections such as candida, mucosal wounds, lesions, ulcers, aphthous ulcers, cold sores, tooth abscesses, and the elimination of mouth malodor resulting from the conditions above and other causes such as microbial proliferation.

Suitable cosmetic and/or therapeutic actives include any material that is generally considered safe for use in the oral cavity and that provides changes to the overall appearance and/or health of the oral cavity. When present, the level of cosmetic and/or therapeutic active in the compositions utilized by the present invention is generally, unless otherwise noted, from about 0.001% to about 90%, in one embodiment from about 0.01% to about 50%, in another embodiment from about 0.1% to about 30%, by weight of the second layer composition. Where the cosmetic and therapeutic actives are in particulate form, a suitable particle size for use in the present invention is from about 0.01 microns to about 1000 microns, in one embodiment from about 0.1 microns to 500 microns, in another embodiment from about 1 to about 100 microns. The following is a non-limiting list of cosmetic and/or therapeutic actives that may be used in the present invention.

The present compositions may comprise at least one anti-calculus (i.e. anti-tartar) agent, present at a level from about 0.001% to about 50%, by weight of the second layer composition, in another embodiment from about 0.01% to about 25%, and in yet another embodiment from about 0.1 to about 15%. The anti-calculus agent should be essentially compatible with the other components of the invention. The anti-calculus agent may be selected from the group consisting of polyphosphates (including pyrophosphates) and salts thereof; polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof. In one embodiment, the salts are alkali metal salts. Polyphosphates are generally employed as their wholly or partially neutralized water-soluble alkali metal salts such as potassium, sodium, ammonium salts, and mixtures thereof. The inorganic polyphosphate salts include alkali metal (e.g. sodium) tripolyphosphate, tetrapolyphosphate, dialkyl metal (e.g. disodium) diacid, trialkyl metal (e.g. trisodium) monoacid, potassium hydrogen phosphate, sodium hydrogen phosphate, and alkali metal (e.g. sodium) hexametaphosphate, and mixtures thereof. Polyphosphates larger than tetrapolyphosphate usually occur as amorphous glassy materials. In one embodiment the polyphosphates are those manufactured by FMC Corporation, which are commercially known as Sodaphos (n≈6), Hexaphos (n≈13), and Glass H (n≈21, sodium hexametaphosphate), and mixtures thereof. The pyrophosphate salts useful in the present invention include, alkali metal pyrophosphates, di-, tri-, and mono-potassium or sodium pyrophosphates, dialkali metal pyrophosphate salts, tetraalkali metal pyrophosphate salts, and mixtures thereof. In one embodiment the pyrophosphate salt is selected from the group consisting of trisodium pyrophosphate, disodium dihydrogen pyrophosphate ($Na_2H_2P_2O_7$), dipotassium pyrophosphate, tetrasodium pyrophosphate ($Na_4P_2O_7$), tetrapotassium pyrophosphate ($K_4P_2O_7$), and mixtures thereof. Polyolefin sulfonates include those wherein the olefin group contains 2 or more carbon atoms, and salts thereof. Polyolefin phosphonates include those wherein the olefin group contains 2 or more carbon atoms. Polyvinylphosphonates include polyvinylphosphonic acid. Diphosphonates and salts thereof include azocycloalkane-2,2-diphosphonic acids and salts thereof, ions of azocycloalkane-2,2-diphosphonic acids and salts thereof, azacyclohexane-2,2-diphosphonic acid, azacyclopentane-2,2-diphosphonic acid, N-methylazacyclopentane-2,3-diphosphonic acid, EHDP (ethane-1-hydroxy-1,1,-diphosphonic acid), AHP (azacycloheptane-2,2-diphosphonic acid), ethane-1-amino-1,1-diphosphonate, dichloromethane-diphosphonate, etc. Phosphonoalkane carboxylic acid or their alkali metal salts include PPTA (phosphonopropane tricarboxylic acid), PBTA (phosphonobutane-1,2,4-tricarboxylic acid), each as acid or alkali metal salts. Polyolefin phosphates include those wherein the olefin group contains 2 or more carbon atoms. Polypeptides include polyaspartic and polyglutamic acids.

Fluoride ion sources are known for use in oral care compositions as anti-caries agents for teeth and may optionally be incorporated within the present invention. Application of fluoride ions to the dental enamel of natural teeth serves to protect those teeth against decay. A wide variety of fluoride ion-yielding materials can be employed as sources of soluble fluoride in the instant compositions. Examples of suitable fluoride ion-yielding materials are found in Briner, et al., U.S. Pat. No. 3,535,421 and Widder, et al., U.S. Pat. No. 3,678,154. Preferred fluoride ion sources for use herein include sodium fluoride, potassium fluoride, stannous fluoride, mono fluoro phosphate (MFP), and ammonium fluoride. In one embodiment sodium fluoride is the fluoride ion source. The instant invention provides from about 5 ppm to 10,000 ppm, in one embodiment from about 100 to 3000 ppm, of fluoride ions in the second layer composition.

The present invention may include a stannous ion source. The stannous ions may be provided from stannous fluoride and/or other stannous salts. Stannous fluoride has been found to help in the reduction of gingivitis, plaque, sensitivity, and in improved breath benefits. The stannous ions provided in an oral composition will provide efficacy to a subject using the composition. Although efficacy could include benefits other than the reduction in gingivitis, efficacy is defined as a noticeable amount of reduction in in situ plaque metabolism. Formulations providing such efficacy typically include stannous levels provided by stannous fluoride and/or other stannous salts ranging from about 3,000 ppm to about 15,000 ppm stannous ions in the total composition. Below about 3,000 ppm stannous the efficacy of the stannous is insufficient. The stannous ion is present in a level of from about 4,000 ppm to about 12,000 ppm, in another embodiment from about 5,000 ppm to about 10,000 ppm. Other stannous salts include organic stannous carboxylates, such as stannous acetate, stannous gluconate, stannous oxalate, stannous malonate, stannous citrate, stannous ethylene glycoxide, stannous formate, stannous sulfate, stannous lactate, stannous tartrate, and the like. Other stannous ion sources include, stannous halides such as stannous chlorides, stannous bromide, stannous iodide and stannous chloride dihydride. In one embodiment the stannous ion source is stannous fluoride in another embodiment, stannous chloride dihydrate. The combined stannous salts may be present in an amount of from about 0.01% to about 11%, by weight of the compositions. The stannous salts may typically be present in an amount of from about 0.1% to about 7%, in one embodiment from about 1% to about 5%, and in yet another embodiment from about 1.5% to about 3%, by weight of the second layer composition.

Anti-microbial agents can also be present in the present invention. Such agents may include, but are not limited to: 5-chloro-2-(2,4-dichlorophenoxy)-phenol, commonly referred to as Triclosan, and described in The Merck Index, 11th ed. (1989), pp. 1529 (entry no. 9573) in U.S. Pat. No. 3,506,720, and in European Patent Application No. 0,251, 591 of Beecham Group, PLC,; 8-hydroxyquinoline and its salts; copper II compounds, including, but not limited to, copper(II) chloride, copper(II) sulfate, copper(II) acetate, copper(II) fluoride and copper(II) hydroxide; phthalic acid and its salts including, but not limited to those disclosed in U.S. Pat. No. 4,994,262, preferably magnesium monopotassium phthalate; chlorhexidine; alexidine; hexetidine; sanguinarine; benzalkonium chloride; salicylanilide; domiphen bromide; cetylpyridinium chloride (CPC); tetradecylpyridinium chloride (TPC); N-tetradecyl-4-ethylpyridinium chloride (TDEPC); octenidine; iodine; sulfonamides; bisbiguanides; phenolics; delmopinol, octapinol, and other piperidino derivatives; nicin preparations; zinc/stannous ion agents; nystatin; grapefruit extracts; apple extracts; thyme oil; thymol; antibiotics such as augmentin, amoxicillin, tetracycline, doxycycline, minocycline, metronidazole, neomycin, kanamycin, and clindamycin; analogs and salts of the above; essential oils including thymol, geraniol, carvacrol, citral, hinokitiol, eucalyptol, catechol (particularly 4-allyl catechol) and mixtures thereof; methyl salicylate; hydrogen peroxide; metal salts of chlorite; and mixtures of all of the above.

The present invention may include an anti-plaque agent such as stannous salts, copper salts, strontium salts, magnesium salts or a dimethicone copolyol. The dimethicone copolyol is selected from C12 to C20 alkyl dimethicone copolyols and mixtures thereof. In one embodiment the dimethicone copolyol is cetyl dimethicone copolyol marketed under the Trade Name Abil EM90. The dimethicone copolyol is generally present in a level of from about 0.001% to about 25%, in one embodiment from about 0.01% to about 5% and in another embodiment from about 0.1% to about 1.5% by weight of the second layer composition.

Anti-inflammatory agents can also be present in the second layer composition of the present invention. Such agents may include, but are not limited to, non-steroidal anti-inflammatory agents oxicams, salicylates, propoionic acids, acetic acids and fenamates. Such NSAIDs include but are not limited to Ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone, phenylbutazone and acetaminophen. Use of NSAIDs such as Ketorolac are claimed in U.S. Pat. No. 5,626,838, issued May 6, 1997. Disclosed therein are methods of preventing and, or treating primary and reoccurring squamous cell carcinoma of the oral cavity or oropharynx by topical administration to the oral cavity or oropharynx of an effective amount of an NSAID. Suitable steroidal anti-inflammatory agents include corticosteroids, such as fluccinolone, and hydrocortisone.

Nutrients may improve the condition of the oral cavity and can be included in the present invention. Nutrients include minerals, vitamins, oral nutritional supplements, enteral nutritional supplements, and mixtures thereof. Useful minerals include calcium, phosphorus, zinc, manganese, potassium and mixtures thereof. Vitamins can be included with minerals or used independently. Suitable vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Oral nutritional supplements include amino acids, lipotropics, fish oil, and mixtures thereof. Amino acids include, but are not limited to L-Tryptophan, L-Lysine, Methionine, Threonine, Levocarnitine or L-carnitine and mixtures thereof. Lipotropics include, but are not limited to, choline, inositol, betaine, linoleic acid, linolenic acid, and mixtures thereof. Fish oil contains large amounts of Omega-3 (N-3) polyunsaturated fatty acids, eicosapentaenoic acid and docosahexaenoic acid. Enteral nutritional supplements include, but are not limited to, protein products, glucose polymers, corn oil, safflower oil, medium chain triglycerides. Minerals, vitamins, oral nutritional supplements and enteral nutritional supplements are described in more detail in *Drug Facts and Comparisons* (loose leaf drug information service), Wolters Kluer Company, St. Louis, Mo., ©1997, pps. 3–17 and 54–57.

A whitening agent may be included as a cosmetic and/or therapeutic active in the second layer composition of the present invention. Such substances are selected from the group consisting of peroxides, metal chlorites, perborates, percarbonates, peroxyacids, persulfates, and combinations thereof. Suitable peroxide compounds include hydrogen peroxide, urea peroxide, calcium peroxide, carbamide peroxide, and mixtures thereof. In one embodiment the peroxide compound is carbamide peroxide. Suitable metal chlorites include calcium chlorite, barium chlorite, magnesium chlorite, lithium chlorite, sodium chlorite, and potassium chlorite. Additional bleaching substances may be hypochlorite and chlorine dioxide. In one embodiment the chlorite is sodium chlorite. In another embodiment the percarbonate is sodium percarbonate. In one embodiment the persulfates are oxones. The level of these substances is dependent on the available oxygen or chlorine respectively that the molecule is capable of providing to bleach the stain. This level is generally used in compositions of the present invention at levels from about 0.01% to about 40%, in one embodiment from about 0.1% to about 20%, in another embodiment from about 0.5% to about 10%, in yet another embodiment form about 4% to about 7% by weight of the second layer composition.

Antioxidants are generally recognized as useful in oral care compositions. Antioxidants are disclosed in texts such as Cadenas and Packer, *The Handbook of Antioxidants,* ©1996 by Marcel Dekker, Inc. Antioxidants that may be included in the compositions used by the present invention include, but are not limited to Vitamin E, ascorbic acid, Uric acid, carotenoids, Vitamin A, flavonoids and polyphenols, herbal antioxidants, melatonin, aminoindoles, lipoic acids and mixtures thereof.

Antiviral actives useful in the second layer composition of the present invention include any known actives that are routinely used to treat viral infections. Such antiviral actives include: but are not limited to, phosphonoformic acid; cyosine derivatives; purine anaglogues, such as adenosine, guanosine and inosine analogues; pyrimidine bases, such as citidine and thymidine; amantadines; rimantadine HCl; ribavirin; zanamivir; oseltamivir phosphate; trifluridine; heterocyclic dyes; acyclovir; famciclovir; valacyclovir, cidofovir; ganciclovir; levimisole; idoxuridine; lipophilic β-ketones; and thiosemicarbazones. These antiviral actives are described in *Drug Facts and Comparisons* (loose-leaf drug information service), Wolters Kluwer Company, St. Louis, Mo., ©2001, pp. 1400–1423(b), and in Kirk-Othmer, *Encyclopedia of Chemical Technology,* Fourth Edition, Volume 3, Wiley-Interscience Publishers (1992), pp. 576–607, both incorporated herein by reference in their entirety. Specific examples include antiviral actives disclosed in U.S. Pat. No. 5,747,070, to Majeti, incorporated herein by reference in its entirety. Said patent discloses the use of stannous salts to control viruses. Stannous salts are described in more detail above. While stannous fluoride may be used as an antiviral agent, it is typically used only in combination with another stannous halide or one or more stannous carboxylates or another therapeutic agent.

Anti-fungal agents can also be included in the second layer composition of the present invention. Anti-fungals are agents that destroy or inhibit the growth of fungi. Anti-fungal agents useful in the present invention are those drugs for systemic mycoses or drugs for mucocutaneuos infections. Suitable antifungals include but are not limited to nystatin; miconazole; econazole nitrate; clotrimazole; and flucytosine. In one embodiment the antifungal agent is nystatin.

Anti-pain or desensitizing agents can also be present in the second layer composition of the present invention. Analgesics are agents that relieve pain by acting centrally to elevate pain threshold without disturbing consciousness or altering other sensory modalities. Such agents may include, but are not limited to, strontium chloride, potassium nitrate, sodium nitrate, sodium fluoride, acetanilide, phenacetin, acertophan, thiorphan, spiradoline, aspirin, codeine, thebaine, levorphenol, hydromorphone, oxymorphone, phenazocine, fentanyl, buprenorphine, butaphanol, nalbuphine, pentazocine, natural herbs such as gall nut, Asarum, Cubebin, Galanga, scutellaria, Liangmianzhen, Baizhi, etc. Anesthetic agents, or topical analgesics, such as acetaminophen, sodium salicylate, trolamine salicylate, lidocaine and benzocaine may also be present. These analgesic actives are described in detail in Kirk-Othmer, *Encyclopedia of Chemical Technology*, Fourth Edition, Volume 2, Wiley-Interscience Publishers (1992), pp. 729–737, incorporated herein by reference in its entirety.

Histamine-2 (H-2 or H2) receptor antagonist compounds (H-2 antagonists) may be used in the present invention. As used herein, selective H-2 antagonists are compounds that block H-2 receptors, but do not have meaningful activity in blocking histamine-1 (H-1 or H1) receptors. Selective H-2 antagonists stimulate the contraction of smooth muscle from various organs, such as the gut and bronchi; this effect can be suppressed by low concentrations of mepyramine—a typical antihistaminic drug. The H-2 antagonists useful in the present invention are those that blockade the receptors involved in mepyramine-insensitive, non-H-1 (H-2), histamine responses and do not blockade the receptors involved in mepyramine-sensitive histamine responses. Selective H-2 antagonists include compounds meeting the above criteria which are disclosed in U.S. Pat. Nos. 5,294,433 and 5,364,616 both to Singer, et al., and assigned to The Procter & Gamble Company, wherein the selective H-2 antagonist is selected from the group consisting of cimetidine, etintidine, ranitidine, ICIA-5165, tiotidine, ORF-17578, lupitidine, donetidine, famotidine, roxatidine, pifatidine, lamtidine, BL-6548, BMY-25271, zaltidine, nizatidine, mifentidine, BMY-25368 (SKF-94482), BL-6341A, ICI-162846, ramixotidine, Wy-45727, SR-58042, BMY-25405, loxtidine, DA-4634, bisfentidine, sufotidine, ebrotidine, HE-30-256, D-16637, FRG-8813, FRG-8701, impromidine, L-643728, and HB-408. Related suitable H-2 antagonists include burimamide and metiamide.

The present invention may also include one or more components that provide fragrance, and/or sensate benefit (warming or cooling agents). Suitable components include menthol, menthyl lactate, wintergreen oil, peppermint oil, spearmint oil, leaf alcohol, camphor, clove bud oil, eucalyptus oil, anethole, methyl salicylate, eucalyptol, cassia, 1-8 menthyl acetate, eugenol, oxanone, alpha-irisone, propenyl guaethol, cinnamon, thymol, linalool, benzaldehyde, cinnamaldehyde glycerol acetal known as CGA, and mixtures thereof, as well as coolants. The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred coolants are selected from the group consisting of menthol, 3-1-menthoxypropane-1,2-diol known as TK-10, manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al. WS-3 and other agents are described in U.S. Pat. No. 4,136,163, Watson, et al. The disclosures of both are herein incorporated by reference in their entirety.

Pigments may be added to the compositions herein to more precisely indicate the locations at which the composition has actually been in contact. Additionally, these substances may be suitable for modifying the color of the denture to satisfy the consumer. These substances comprise particles that when applied on the tooth surface modify that surface in terms of absorption and, or reflection of light. Such particles provide an appearance benefit when a film containing such particles is applied over the surfaces of the denture. Pigments, dyes, colorants and lakes may also be added to modify the appearance of the compositions herein to render the product more acceptable to the consumer. Appropriate pigment levels are selected for the particular impact that is desirable to the consumer. For example, for dentures that are particularly dark or stained one would typically use pigments in sufficient amounts to lighten the teeth. On the other hand, where individual teeth or spots on the teeth are lighter than other teeth, pigments to darken the denture may be useful. The levels of pigments and colorants may be in the range of about 0.001% to about 20%, in one embodiment from about 0.01% to about 15% and in another embodiment from about 0.1% to about 10% by total weight of the composition.

Pigments and colorants include inorganic white pigments, inorganic colored pigments, pearling agents, filler powders and the like; see Japanese Published Patent Application Kokai No. 9 [1997]-100215, published Apr. 15, 1997, incorporated herein by reference. Specific examples are selected from the group consisting of talc, mica, magnesium carbonate, calcium carbonate, magnesium silicate, aluminum magnesium silicate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures thereof. In one embodiment the pigments and colorants are those selected from the group consisting of titianium dioxide, bismuth oxychloride, zinc oxide, Opatint D&C Red 27, CI 16185:1 Acid 27 Lake E123, C114720:1 Carmosoisine Aluminum Lake E122, Red 7 Lake, or Red 30 Lake, and mixtures thereof.

Additional actives suitable for use in the present invention may include, but are not limited to, insulin, steroids, herbal and other plant derived remedies, and anti-neoplastics. Additionally, anti-gingivitis or gum care agents known in the art may also be included. Components, other than polybutene, which impart a clean feel to the teeth may optionally be included. These components may include, for example, baking soda or Glass-H. Also, it is recognized that in certain forms of therapy, combinations of these above-named agents may be useful in order to obtain an optimal effect. Thus, for example, an anti-microbial and an anti-inflammatory agent may be combined in a single second layer composition to provide combined effectiveness.

The second layer composition utilized by the present invention may further comprise a viscosity modifier that inhibits settling and separation of components or controls settling in a manner that facilitates re-dispersion and may control flow properties. A viscosity modifier is particularly useful to keep cosmetic and/or therapeutic actives that are in particulate form suspended within the polybutene components of the compositions used by the present invention. Suitable viscosity modifiers herein include mineral oil, organo modified clays, petrolatum, silicas, and mixtures thereof. In one embodiment the viscosity modifier is silica. Where incorporated, the viscosity modifier is present in the polybutene component of the present invention at a level of from about 0.001% to about 30%, in one embodiment from about 0.01% to about 10%, and in another embodiment from about 0.1% to about 3% of the second layer composition.

The second layer composition may optionally further comprise one or more flavorants. These flavoring agents can be chosen from synthetic flavoring liquid and/or oils derived from plants leaves, flowers, fruits and so forth, and combinations thereof. Representative flavoring liquids include: vanillin, sage, marjoram, parsley oil, spearmint oil, cinnamon oil, oil of wintergreen (methylsalicylate), peppermint oils clove oil, bay oil, anise oil, and eucalyptus oil. Also useful are artificial, natural or synthetic fruit flavors such as citrus oil including lemon, orange, banana, grape, lime, apricot and grapefruit and fruit essences including apple, strawberry, cherry, orange, pineapple and so forth; bean and nut derived flavors such as coffee, cocoa, cola, peanut, almond and so forth. Additionally, flavor adsorbed onto a hydrophilic matrix may be included, e.g. "spray-dried" flavors. Furthermore, encapsulated flavors may be included. The amount of flavorant employed is normally a matter of preference subject to such factors as flavor type and strength of flavor desired. Flavorants may be present in amounts up to about 4%, in one embodiment about 0.05% to about 3.0%, in another embodiment about 0.8% to about 2.5%, by weight of the total composition.

The present compositions may further comprise sweeteners. Suitable sweeteners include natural and artificial, water soluble, water insoluble and intense sweeteners. The sweetening agent may be dextrose, sucrose, maltose, dextrin, dried invert sugar, mannose, xylose, ribose, glucose, fructose, levulose, galactose, corn syrup, high fructose corn syrup, corn syrup solids, partially hydrolyzed starch, aspartame, saccharin, sugar alcohols such as sorbitol, mannitol, xylitol, maltitol, isomalt, and hydrogenated starch hydrolysate or combinations thereof. Natural or artificial intense sweeteners such as dipeptide based intense sweeteners, monellin, thaumaoccous danielli, and L-aspartyl L-phenylalanine methyl ester and soluble saccharin salts may also be incorporated as sweeteners. The amount of the sweetener will vary with the type of sweetener selected and the desired level of sweetness. Sweetening agents and flavoring agents are typically used in oral care compositions at levels of from about 0.005% to about 5%, by weight of the composition.

Oral Care Carriers

It may be desirable to add one or more oral care carriers to the second layer composition. Water may be incorporated within the second layer composition and should preferably be of low ion content and free of organic impurities.

The second layer composition may optionally further comprise one or more flavorants. These flavoring agents can be chosen from synthetic flavoring liquid and/or oils derived from plants leaves, flowers, fruits and so forth, and combinations thereof. Representative flavoring liquids include: vanillin, sage, marjoram, parsley oil, spearmint oil, cinnamon oil, oil of wintergreen (methylsalicylate), peppermint oils clove oil, bay oil, anise oil, and eucalyptus oil. Also useful are artificial, natural or synthetic fruit flavors such as citrus oil including lemon, orange, banana, grape, lime, apricot and grapefruit and fruit essences including apple, strawberry, cherry, orange, pineapple and so forth; bean and nut derived flavors such as coffee, cocoa, cola, peanut, almond and so forth. Additionally, flavor adsorbed onto a hydrophilic matrix may be included, e.g. "spray-dried" flavors. Furthermore, encapsulated flavors may be included. The amount of flavorant employed is normally a matter of preference subject to such factors as flavor type and strength of flavor desired. Flavorants may be present in amounts up to about 4%, in one embodiment about 0.05% to about 3.0%, in another embodiment about 0.8% to about 2.5%, by weight of the total composition.

The present compositions may further comprise sweeteners. Suitable sweeteners include natural and artificial, water soluble, water insoluble and intense sweeteners. The sweetening agent may be dextrose, sucrose, maltose, dextrin, dried invert sugar, mannose, xylose, ribose, glucose, fructose, levulose, galactose, corn syrup, high fructose corn syrup, corn syrup solids, partially hydrolyzed starch, aspartame, saccharin, sugar alcohols such as sorbitol, mannitol, xylitol, maltitol, isomalt, and hydrogenated starch hydrolysate or combinations thereof. Natural or artificial intense sweeteners such as dipeptide based intense sweeteners, monellin, thaumaoccous danielli, and L-aspartyl L-phenylalanine methyl ester and soluble saccharin salts may also be incorporated as sweeteners. The amount of the sweetener will vary with the type of sweetener selected and the desired level of sweetness. Sweetening agents and flavoring agents are typically used in oral care compositions at levels of from about 0.005% to about 5%, by weight of the composition.

The present invention may also comprise surfactants, commonly referred to as sudsing agents. Suitable surfactants are those that are reasonably stable and foam throughout a wide pH range. The surfactants are present at a level of from about 0.001% to about 12%, in one embodiment from about 0.01% to about 8%, and in another embodiment from about 0.1% to about 6%, by weight of the oral care carrier component of the oral care composition. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauryl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed in U.S. Pat. No. 3,959,458, to Agricola, et al., incorporated herein in its entirety by reference. Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene sorbitan esters (sold under trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed in U.S. Pat. No. 4,051,234, Gieske, et al., incorporated herein by reference in its entirety.

Additional oral care carriers suitable for use in the second layer composition include: abrasive polishing materials such as silica gels and precipitates, aluminas and phosphates; alkali bicarbonate salts, such as sodium bicarbonate; buffering agents such as monosodium phosphate, sodium hydroxide, potassium hydroxide, sodium carbonate and imidazole; acidic compounds; thickening agents; humectants; and xylitol.

III. The Release Liner

The release liner may be formed from any material which exhibits less affinity for the second layer composition than the second layer composition exhibits for itself and for the first layer strip of material. The release liner may comprise a rigid sheet of material such as polyethylene, paper, polyester, or other material, which is then coated with a nonstick type material. The release liner may be cut to substantially the same size and shape as the strip of material or the release liner may be cut larger than the strip of material to provide a readily accessible means for separating the material from the strip. The release liner may be formed from a brittle material that cracks when the strip is flexed or from multiple pieces of material or a scored piece of material. Alternatively, the release liner may be in two overlapping pieces such as a typical adhesive bandage design. A description of materials suitable as release agents is found in Kirk-Othmer, Encyclopedia of Chemical Technology, Fourth Edition, Volume 21, pp. 207–218, incorporated herein by reference.

Method of Preparation

In the above described delivery system, the second layer composition is suitably made as follows: Combine the polybutene and the cosmetic or therapeutic actives into a mixing vessel and mix well with any means known within the art, for example, with spatula or mixer. Heat the composition, if desired, to facilitate mixing. Continue mixing the composition until homogenous. Where the cosmetic or therapeutic active is included in solid particulate form, the addition of a viscosity modifier, such as silica, may be appropriate to keep the particulate dispersed and suspended within the composition. Flavorants or sweeteners and other oral care carriers may also be added to the second layer composition by mixing as desired.

The integral carrier material, such as a strip, may be formed by several of the film making processes known in the art. In one embodiment a strip of polyethylene is made by a blown process or a cast process. Other processes including extrusion or processes that do not affect the flexural rigidity of the strip of material are also feasible. Additionally, the second layer composition may be incorporated onto the strip during the processing of the strip. The second layer composition may be a laminate on the strip.

Method of Use

Where the integral carrier is a strip of material, the second layer composition may be coated on the strip of material, or be applied by the user to the strip of material, or be applied by the user to the teeth and then the strip of material placed over the coated teeth. The amount of the second layer composition applied to the strip of material or teeth will depend upon the size and capacity of the piece of material, concentration of the active and the desired benefit. Generally less than 1 gram of substance is required, preferably from about 0.05 grams to about 0.5 grams and more preferably from about 0.1 gram to about 0.4 grams of substance is used. The amount of composition per square centimeter (cm) of material is less than about 1 gram/cm$^2$, preferably less than about 0.2 grams/cm$^2$, more preferably 0.005 grams/cm$^2$ to about 0.1 grams/cm$^2$, and yet more preferably from about 0.01 grams/cm$^2$ to about 0.04 grams/cm$^2$.

The optimal time and frequency of application will depend on the desired cosmetic or therapeutic effect, the severity of any condition being treated, the heath of the user and like considerations. For example, the strip may be worn from about from about 5 minutes up to 12 hours, more preferably from about 5 minutes up to about 120 minutes, per application and may be applied from about 1 to about 7 times per day. The duration and frequency of application will depend on a number of factors, i.e. the severity of the condition, the age and health of the wearer, etc. Additionally, the length of treatment to achieve the desired benefit, for example, tooth whitening, may last from about one day to about six months, more preferably from about one day to about 28 days, and most preferably from about 7 to about 28 days. Due to the high degree of substantivity of the polybutene to the teeth, the polybutene may continue to adhere to the teeth for a prolonged period of time after the strip has been removed.

It is not necessary to prepare the oral cavity before applying the composition of the present invention. The surfaces of the oral cavity are neither required to be dried nor to be excessively wet with saliva or water before the composition is applied. However, it is believed that adhesion to the tooth surfaces will be improved if the surfaces are dry when the composition is applied.

The above-described delivery systems may be combined in a kit which comprises one or more strip means and instructions for use.

EXAMPLES

The following non-limiting examples further illustrate and describe the embodiments of the subject invention wherein both essential and optional ingredients are combined. It is to be understood that the examples are given solely for the purpose of illustration and are not to be construed as limiting the scope of the present invention, as many variations thereof are possible without departing from the spirit and scope of the invention.

In the examples below, the second layer composition is prepared as follows: The polybutene is combined with the cosmetic or therapeutic active into a mixing vessel and mixed well with a mechanical mixer. The composition is mixed until homogenous. Where the cosmetic or therapeutic active is in solid particulate form, a viscosity modifier, such as silica, may be added to the mixture in the same manner and mixing continues until homogenous. Values given below are in weight percent of the total second layer composition.

Examples 1–6

| Ingredients | Ex. 1 | Ex. 2 | Ex. 3 | Ex. 4 | Ex. 5 | Ex. 6 |
|---|---|---|---|---|---|---|
| Polybutene[1] | 87% | 99.7% | 99.742% | 99.56% | 99.84% | 75.00% |
| Glass-H | | 13% | | | | 25.00% |
| Triclosan | | 0.3% | | | | |
| Thymol | | | 0.064% | | | |
| Eucalyptol | | | 0.092% | | | |
| Menthol | | | 0.060% | 0.12% | | |
| Methyl Salicylate | | | 0.042% | | | |
| Menthyl Lactate | | | | 0.17% | | |
| Peppermint | | | | 0.15% | | |
| 8-hydroxy-quinoline salts | | | | | 0.10% | |
| $CuCl_2 \cdot 2H_2O$ | | | | | | 0.06% |

[1]Indopol H-300, MW = 1330, trade name of BP Amoco Chemicals (Chicago, IL).

Examples 7–12

| Ingredients | Ex. 7 | Ex. 8 | Ex. 9 | Ex. 10 | Ex. 11 | Ex. 12 |
|---|---|---|---|---|---|---|
| Polybutene[2] | 90% | 80% | 99.955% | 99.757% | 99.97% | 99.1% |
| CPC | | | 0.045% | | | 0.09% |
| Apple Extract | 10% | | | | | |
| Baking Soda | | 20% | | | | |
| Sodium Fluoride | | | | 0.243% | | |
| Nystatin | | | | | 0.03% | |

[2]Indopol H-40, MW = 750, trade name of BP Amoco Chemicals (Chicago, IL).

Examples 13–19

| Ingredients | Ex. 13 | Ex. 14 | Ex. 15 | Ex. 16 | Ex. 17 | Ex. 18 | Ex. 19 |
|---|---|---|---|---|---|---|---|
| Polybutene[3] | | 90% | 90% | 90% | 99.76% | 99.76% | 99.066% |
| Carvacrol | | 10% | | | | | |
| Grape Seed Extract | | | 10% | | | | |
| Opatint D&C Red 27 | | | | 0.24% | | | |
| Red 7 | | | | | 0.24% | | |
| Red 30 | | | | | | 0.24% | |
| Grapefruit Seed Extract | | | | 10% | | | |
| Calcium Peroxide | | | | | | | 0.934% |

[3]Indopol 11-100, MW = 940, trade name of BP Amoco Chemicals (Chicago, IL).

Examples 20–25

| Ingredients | Ex. 20 | Ex. 21 | Ex. 22 | Ex. 23 | Ex. 24 | Ex. 25 |
|---|---|---|---|---|---|---|
| Polybutene[4] | 90% | 99% | 99.47% | 97.95% | 99.24% | 92.5% |
| Xylitol | 10% | | | | | |
| Chlorexidine | | 1% | | | | |
| Stannous Fluoride | | | 0.53% | | | |
| Tetra Sodium Pyrophosphate | | | | 2.05% | | |
| Eugenol | | | | | | 7.5% |
| Mono Fluoro Phosphate | | | | | 0.76% | |

[4]Indopol H-1900, MW = 2270, trade name of BP Amoco Chemicals (Chicago, IL).

Examples 26–33

| Ingredients | Ex. 26 | Ex. 27 | Ex. 28 | Ex. 29 | Ex. 30 | Ex. 31 | Ex. 32 | Ex. 33 |
|---|---|---|---|---|---|---|---|---|
| Polybutene[5] | 81% | 81% | 81% | 80% | 56% | 80% | 81% | 100% |
| Sodium Percarbonate | 19% | | | | 19% | 19% | | |
| Urea Peroxide | | 19% | | | | | | |
| Calcium Peroxide | | | 19% | | | | | |
| Silica | | | | 1% | | | | |
| Petrolatum | | | | | 25% | | | |
| Benzocaine | | | | | | 20% | | |
| (Polyvinyl-Pyrrolidone) Peroxide Complex | | | | | | | 19% | |

[5]Indopol H-300, MW = 1330, trade name of BP Amoco Chemicals (Chicago, IL).

Examples 34–37

| Ingredients | Ex. 34 | Ex. 35 | Ex. 36 | Ex. 37 |
|---|---|---|---|---|
| Polybutene[6] | 63.76% | 54.5% | 60.5% | 61.5% |
| Petrolatum | 10.00% | 12.5% | 12.5% | 12.5% |
| Silica | 1.00% | 1.0% | 1.0% | 1.0% |
| Glass-H | 25.00% | 25.0% | 25.0% | 25.0% |
| Peppermint Oil | | 6.0% | | |

-continued

| Ingredients | Ex. 34 | Ex. 35 | Ex. 36 | Ex. 37 |
|---|---|---|---|---|
| Asparatame | | 1.0% | 1.0% | |
| Opatint 27 | 0.24% | | | |

<sup>e</sup>Indopol H-300, MW = 1330, trade name of BP Amoco Chemicals (Chicago, IL).

The second layer composition is applied onto the strip of material. The second layer may form a coating comprising a uniform continuous layer on the strip. Alternatively, the second layer may be a laminate or separated layers of components, an amorphous mixture of components, separate stripes or spots or other patterns of different components, or a combination of these structures The above describes one embodiment of the present invention. Also contemplated is the use of the strip of material as an applicator means for applying the second layer composition to the teeth, then removing the strip material. The second layer material exhibits sufficient substantivity to achieve prolonged release of the cosmetic and therapeutic actives in the oral cavity without the strip means remaining in the mouth. Also contemplated by the present invention is a water permeable bag like structure, in the shape of a strip or patch that contains and releases cosmetic and therapeutic actives in the oral cavity over time and may be fixed in place by the second layer composition of the present invention.

It is understood that the examples and embodiments described herein are for illustrative purposes only and that various modifications or changes in light thereof will be suggested to one of skill in the art without departing from the scope of the present invention.

What is claimed is:

1. A delivery system for delivering oral care actives to oral surfaces comprising:
   a) an integral carrier, and
   b) a composition comprising polybutene with a molecular weight of about 300 to about 3000 and one or more cosmetic or therapeutic actives, releasably associated with the integral carrier.

2. The delivery system according to claim 1 wherein the amount of said composition is less than about 0.2 grams/cm$^2$.

3. The delivery system according to claim 1 wherein said integral carrier is in the form of a flexible strip of material having sufficient flexibility to form a curved shape on an oral surface, said strip of material being conformable to the oral surface without permanent deformation when said delivery system is placed thereagainst and wherein said flexible strip of material comprises a first side and a second side and wherein said composition is applied to said second side of said flexible strip of material.

4. The delivery system according to claim 3 further comprising a release liner.

5. The delivery system according to claim 3 wherein the flexible strip of material has a width of about 0.5 to about 4 centimeters.

6. The delivery system according to claim 3 wherein the flexible strip of material has a length of about 2 cm to about 12 centimeters.

7. The delivery system according to claim 3 wherein the flexible strip of material further comprises a plurality of pockets.

8. The delivery system according to claim 3 wherein the flexible strip of material has a thickness of less than 1 millimeter.

9. The delivery system according to claim 1 wherein the polybutene has a molecular weight of about 500 to about 2200.

10. The delivery system according to claim 9 wherein the polybutene has a molecular weight of about 750 to about 1500.

11. The delivery system according to claim 1 wherein the cosmetic or therapeutic active comprises a unit dose.

12. The delivery system according to claim 11 wherein the cosmetic or therapeutic active is selected from the group consisting of anti-calculus agents, fluoride ion sources, stannous ion sources, whitening agents, anti-microbial and anti-plaque agents, anti-inflammatory agents, nutrients, antioxidants, anti-viral agents, anti-fungal agents, analgesic and anesthetic agents, H-2 antagonists, components other than polybutene which deliver a clean feel to the teeth, fragrances and sensates, pigments and colorants, and mixtures thereof.

13. The delivery system according to claim 12 wherein the cosmetic or therapeutic active is selected from the group consisting of triclosan, baking soda, sodium fluoride, potassium nitrate, sodium nitrate, nystatin, grapefruit seed extract, stannous fluoride, tetra sodium pyrophosphate, mono fluoro phosphate, Opatint D&C Red 27, polyphosphates, peroxides and cetylpyridinium chloride.

14. The delivery system according to claim 13 wherein the peroxide is carbamide peroxide.

15. The delivery system according to claim 1 wherein the composition further comprises a viscosity modifier.

16. A oral care product comprising:
   a) a package; and
   b) one or more delivery systems for delivering oral care actives to oral surfaces comprising: an integral carrier, and a composition comprising polybutene with a molecular weight of about 300 to about 3000 and one or more cosmetic or therapeutic actives, releasably associated with the integral carrier, disposed within said package.

17. A method of providing sustained release of therapeutic and cosmetic actives to oral surfaces comprising delivering with an integral carrier a composition comprising polybutene with a molecular weight of about 300 to about 3000, and a cosmetic or therapeutic active, to said oral surfaces.

18. The method according to claim 17 wherein the integral carrier is a strip of material.

19. The method according claim 18 wherein the cosmetic or therapeutic active is a whitening agent.

20. The method according of claim 19 wherein the whitening agent is carbamide peroxide.

21. A method of inhibiting or reducing gingivitis, caries, staining, fungi, bacteria and plaque build up on oral surfaces comprising delivering with an integral carrier a composition comprising polybutene with a molecular weight of about 300 to about 3000, and a cosmetic or therapeutic active, to said oral surfaces.

22. The method according to claim 21 wherein the integral carrier is a strip of material.

23. A method of imparting a clean feel to oral surfaces comprising delivering with an integral carrier a composition comprising polybutene with a molecular weight of about 300 to about 3000, and a cosmetic or therapeutic active, to said oral surfaces.

24. The method according to claim 23 wherein the integral carrier is a strip of material.

* * * * *